(12) United States Patent
Beaumont et al.

(10) Patent No.: US 8,215,836 B2
(45) Date of Patent: Jul. 10, 2012

(54) PHANTOM OBJECT FOR THE QUALITY CONTROL OF A DEVICE FOR RADIATION THERAPY TREATMENT AND METHODS FOR ITS MANUFACTURE AND ITS USE

(75) Inventors: Stephane Beaumont, Nieul le Dolent (FR); Margit Villing, Nieul le Dolent (FR); Yves Barbotteau, Marseilles (FR); Rachid Boucenna, La Roche sur Foron (FR)

(73) Assignee: Qualiformed Sarl, La Roche-sur-Yon (FR)

( * ) Notice: Subject to any disclaimer, the term of this patent is extended or adjusted under 35 U.S.C. 154(b) by 185 days.

(21) Appl. No.: 12/792,105

(22) Filed: Jun. 2, 2010

(65) Prior Publication Data
US 2010/0303210 A1    Dec. 2, 2010

(30) Foreign Application Priority Data
Jun. 2, 2009    (FR) ...................................... 09 53644

(51) Int. Cl.
*G01D 18/00*    (2006.01)
(52) U.S. Cl. ...................................................... 378/207
(58) Field of Classification Search ................... 378/65, 378/62, 207
See application file for complete search history.

(56) References Cited

U.S. PATENT DOCUMENTS

| | | | |
|---|---|---|---|
| 5,281,232 A | 1/1994 | Hamilton et al. | |
| 6,044,132 A * | 3/2000 | Navab | 378/163 |
| 6,379,043 B1 * | 4/2002 | Zylka et al. | 378/207 |
| 6,670,618 B1 | 12/2003 | Hartmann et al. | |
| 2004/0005035 A1 * | 1/2004 | White et al. | 378/207 |
| 2005/0013406 A1 | 1/2005 | Dyk et al. | |
| 2005/0094771 A1 * | 5/2005 | Basu et al. | 378/207 |
| 2006/0002519 A1 | 1/2006 | Jenkins et al. | |
| 2007/0071176 A1 * | 3/2007 | Main et al. | 378/207 |
| 2007/0284543 A1 | 12/2007 | Rockseisen | |
| 2008/0049412 A1 | 2/2008 | Suh et al. | |
| 2008/0240364 A1 * | 10/2008 | Main et al. | 378/207 |

FOREIGN PATENT DOCUMENTS

| | | |
|---|---|---|
| DE | 19907065 A1 | 8/2000 |
| EP | 1854412 A | 11/2007 |

OTHER PUBLICATIONS

French Search Report in Corresponding Application No. FA 722076/FR 0953644 Dated Nov. 20, 2009.

* cited by examiner

*Primary Examiner* — Irakli Kiknadze
(74) *Attorney, Agent, or Firm* — Young & Thompson (57) ABSTRACT

This phantom object is designed for a Winston-Lutz test on a device for radiation therapy treatment comprising a patient support having a rotation axis (V), a stand having a rotation axis (H) and a collimator having a rotation axis (C), locating means being provided for visually representing the theoretical positions (V', H', C') of the three axes (V, H, C). A spherical ball is positioned at the center of a sphere in a material of electron density lower than that of the ball, the ball and the sphere both constituting the phantom object. The sphere has on its outer surface means for a visual alignment with the locating means allowing a positioning of the phantom object at the point of convergence of the three axes (V', H', C').

19 Claims, 3 Drawing Sheets

PHANTOM OBJECT FOR THE QUALITY CONTROL OF A DEVICE FOR RADIATION THERAPY TREATMENT AND METHODS FOR ITS MANUFACTURE AND ITS USE

CROSS-REFERENCE TO RELATED APPLICATIONS

Applicant claims priority under 35 U.S.C. 119 of French patent application No. 0953644 filed on Feb. 6, 2010.

BACKGROUND OF THE INVENTION

The present invention relates to a phantom object (also referred to as test object) for the quality control of devices for radiation therapy treatment, to a method for the manufacture of the phantom object and to methods of use of this phantom object, consisting in a method of checking the coincidence, the orthogonality and the spatial position of locating means of the three theoretical axes of rotation of a device for radiation therapy treatment and in a method of searching the isocenter of a device for radiation therapy treatment using the phantom object, the latter being the two aspects of quality control.

Treatment by radiation therapy for the treatment of cancer should be performed so that the rays are targeted on the tumor and avoid to the maximum extent healthy tissue around the treated tumor.

To ensure the targeting of the rays on the tumor, several quality control tests of the treatment devices have been developed, which are performed on the treatment device before the radiation therapy treatment of a patient.

Figure 3:
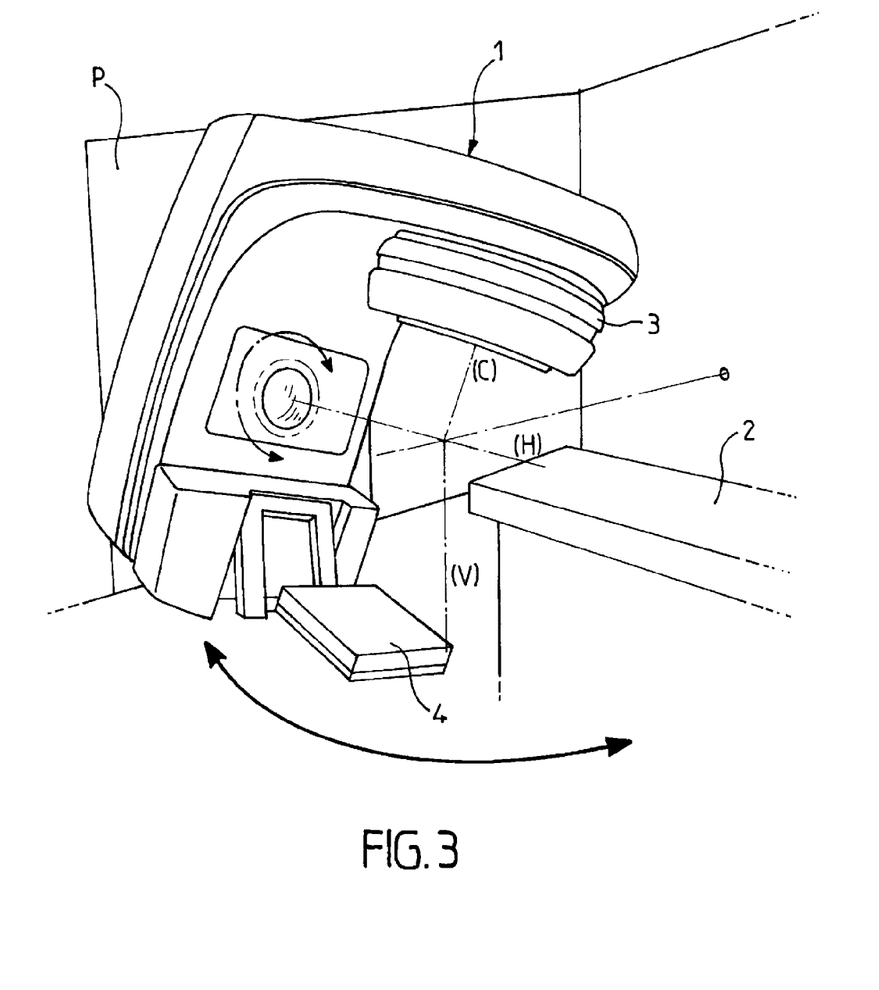
FIG. 3 is a schematic view of a device for radiation therapy treatment with which the phantom object of the present invention is used to perform a W&L test, wherein the three real axes of rotation of the device are shown.

A conventional device for radiation therapy treatment, shown for example in FIG. 3, comprises a stand, bearing at one end an irradiation head which ends by a collimator which allows to delineate the radiation beam (or irradiation beam) and at the other end an imager referred to as portal imager which allows to make digital radiographies of an object positioned between the collimator and the imager, generally on a treatment table also referred to as patient support.

The treatment device comprises three axes of rotation, shown on FIG. 3: the horizontal axis of rotation of the stand, which allows the rotation of the irradiation head around the treated patient, the axis of rotation of the collimator, which is an axis passing by the center of the collimator, and perpendicular to the horizontal axis of rotation of the stand, this axis being coincident with the vertical axis passing by the center of the collimator when the rotation angle of the stand is null, and the vertical axis of rotation of the patient support, which is an axis passing by the center of the collimator, when the rotation angle of the stand is null.

The point of convergence of these three axes is called the isocenter.

The position and the "size" of this isocenter are crucial to be known because it is on this point, in the three-dimensional space of the treatment room, that the center of the tumor to be treated will be positioned, so that it can be irradiated by means of multiple concentric beams. This isocenter point is represented physically in the treatment rooms by five orthogonal laser layers, two frontal, one sagittal and two transverse. These layers will allow the alignment of three reference points (one anterior and two lateral) represented physically on the patient skin (tattoo) or on the surface of a restraining system used for positioning very precisely the patient, during the phase of preparation and planning of the treatment.

Both transverse layers are ideally in a vertical plane, orthogonal to the longitudinal direction of the patient support when its rotation angle is null, while the two frontal layers are ideally in a horizontal plane, and the sagittal layer is in a vertical plane, orthogonal to the plane of the transverse layers.

In order to ensure the geometrical precision of the irradiation, it is of primary importance to check the proper alignment of the theoretical isocenter represented physically by the intersection of the locating laser layers with the real isocenter of the treatment device, which corresponds to the intersection of the three real axes of rotation of the device for radiation therapy treatment. Any misaligning between the real isocenter and the theoretical isocenter would result, on the one hand, in an incomplete irradiation of the tumor, which can induce a resurgence of the disease, and, on the other hand, in an irradiation of the healthy tissue around the tumor, said irradiation being liable to produce severe complications.

Winston-Lutz (W&L) test allows checking the coincidence of the theoretical isocenter and of the real isocenter. It consists in aligning a radio-opaque ball, therefore of high electron density, especially of a density close to the one of a metal, spherical (mostly in steel) on the theoretical isocenter of the device (intersection of the locating laser layers), and in performing multiple radiographies of this object with the X-rays from the treatment beams. By performing such radiographies for different rotation angles of the stand, the position and the "size" of the axis of rotation of the stand is determined. By performing these radiographies for different rotation angles of the patient support, the position and the "size" of the axis of rotation of the patient support is determined. Finally, by performing these radiographies for different rotation angles of the collimator, the position and the "size" of the axis of rotation of the collimator is determined. It should be noted that, during the W&L test, a series of radiographies is performed around a single axis of rotation at a time, while the other rotation angles around the two other axes are set to 0°. The angle of 0° for the stand corresponds to the vertical position thereof (as shown on FIG. 4), the angle of 0° for the patient support corresponds to the position of the patient support in which the longitudinal direction of the patient support is aligned with the axis of rotation of the stand, and the angle of 0° for the collimator corresponds to a preset angle in the collimator. This Winston-Lutz test is described on the Web page http://www.wienkav.at/kav/kfj/91033454/physik/aS500/aS500_sphere.htm The word "size" used to define a feature of an axis of rotation, as used above for the real axes of rotation, corresponds to the mean diameter of the considered axis of rotation, which, in the case of the real axes of rotation, does not correspond exactly to a line, but is contained in a very thin cylinder.

If a phantom object consisting of a radio-opaque ball is perfectly positioned on the real isocenter of the device, which means that the theoretical isocenter (locating means) matches perfectly with the real isocenter of the treatment device, then the image of the ball on the recurrent radiographies is constant.

Otherwise, the image of the radio-opaque ball follows a movement, the analysis of which allows to find the shifts to be produced in order to realign the theoretical isocenter on the real isocenter of the treatment device.

The radio-opaque ball should be sufficiently small-sized so that it can be contained in an irradiation beam of small section (about 50 mm) delineated by the collimator. Indeed, the movements of the radio-opaque ball are not studied with respect to an origin related to the radiation detector, but with respect to the center of the irradiation beam detected on the radiation detector. Indeed, this allows overcoming a possible movement of the radiation detector during the rotation of the rotating stand, this movement being interpreted as a defect on the isocenter of the treatment device. In order to limit also a possible movement with the rotation of the stand of the system of limitation of the beam contained in the collimator, small section beams are used. Several phantom objects exist for performing the W&L test. The most used phantom object is a radio-opaque ball with a diameter between 2 or 10 mm, which has to be aligned on the five locating laser layers. This procedure is difficult because, generally, the ball cannot bear alignment marks with the laser layers because of its small size. Even if it was engraved, still because of its small size, the alignment of the lasers can be controlled only on a reduced surface of the ball, which results in an inaccuracy in positioning the ball of about the shifts between the real and theoretical isocenters which are to be measured and corrected. A solution would consist in a further reduction of the size of the ball to make more accurate the laser alignment, but in this case, it would be difficult to locate the less and less opaque ball in the recurrent radiographies.

Other phantom objects rely on the principle consisting in enclosing the ball in a plastics parallelepiped with small sizes (20 cm$^3$) comprising a reticule engraved on three of the six faces, the anterior face and the two lateral faces. This time, the alignment of the ball is facilitated but the parallelepiped geometry makes the recurrent radiographies disparate because of the variations of the image of the projection of the parallelepiped with the projection angle. This disadvantage prevents an optimal detection of the center of the radio-opaque ball, especially with the use of software of automatic analysis of the radiographies. Moreover, the parallelepiped geometry prevents from checking the coincidence of the laser layers and the small sizes of the encompassing parallelepiped limit the accuracy of the prior control of the orthogonality and of the spatial position (horizontality and verticality) of the laser layers.

Thus, the currently used phantom object exhibit two major disadvantages: on the one hand, the inaccuracy of the positioning of the radio-opaque ball at the intersection of the five laser layers, i.e. on the theoretical isocenter, and on the other hand, the impossibility to check, prior or complementary to the W&L test, the orthogonality, the coincidence and the spatial position of the laser layers, therefore of the three theoretical axes.

Indeed, two of the three theoretical axes (the axis of rotation of the collimator and of the patient support) must be vertical, and the last theoretical axis (axis of rotation of the stand) must be horizontal.

BRIEF SUMMARY OF THE INVENTION

The present invention overcomes the disadvantages of the phantom objects of the prior art, and relates to a phantom object for a quality control test of a device for radiation therapy treatment, wherein said device for radiation therapy treatment comprises:
  a patient support for positioning a patient for a radiation therapy treatment of the patient, wherein said patient support is rotationally movable around a vertical axis (V);
  a stand supporting at one end the irradiation head which ends by a collimator allowing to delineate a radiation beam and, at the other end means for detecting a radiation, wherein the stand is rotationally movable around an horizontal axis of rotation (H), the collimator is rotationally movable around an axis (C) parallel to the direction of the emitted beam and passing by the center of the collimator,
  wherein locating means external to and/or supported by the device for radiation therapy are provided to represent visually the theoretical positions (V', H', C') of the three axes (V, H, C), the quality control test comprising the step of imaging successively a spherical ball made of a material with an electron density d1, and positioned at the point of convergence of the theoretical axes (V', H', C'),
characterized in that the spherical ball of electron density d1 is positioned at the center of a sphere made of a material with an electron density d2 to constitute together the phantom object, wherein the diameter section of said ball is lower than the section of said radiation beam and the diameter section of said sphere is larger than the section of said radiation beam, the ratio of the electron density d1 on the electron density d2 being higher or equal to 1.1, and wherein said sphere bears on its outer surface visual alignment means with the locating means allowing a positioning of the phantom object, so that said spherical ball is properly positioned at the point of convergence of the three axes (V', H', C'), said sphere being provided with means allowing to secure it to means of placing of the phantom object on the device for radiation therapy treatment.

This quality control test is the Winston-Lutz test described above.

The diameter section of a ball of a sphere is defined as the section of this ball or of this sphere along one of its diameters.

The electron density of a material is defined as the number of electrons contained by cubic centimeter. It can be expressed with respect to water. It is computed as the product of: Density of the material (g/cm$^3$)*Avogadro Number (6.0228 10$^{23}$ atoms/mole)*Z (Atomic number of the material)/A (atomic weight of the material).

This electron density is often expressed with respect to that of water (relative electron density).

In the following, the relative electron density of a material will mean the electron density of this material with respect to that of water, or electron density of the material divided by the electron density of water (~3.34 10$^{23}$ electrons/cm$^3$).

The electron density ratios between the material of electron density d1 and the material of electron density d2 (d1/d2) are advantageously between 2 and 20, more preferably 12.

An electron density ratio between the material of electron density d1 and the material of electron density d2 of 12 yields optimal results for the quality control test.

The measurements of the position of the image of the ball of electron density d1 on the radiation detector are performed with respect to the image of the radiation beam on the detector, the position of the ball being detected with respect to the image of the edges of the beam on the detector.

The electron density of the ball (d1) is higher than the electron density of the sphere (d2) so that there is a contrast of electron density between the ball and the sphere. As the radio-opacity of a material is an increasing function with respect to the electron density of this material, the ball (of higher electron density) is more radio-opaque than the sphere (of lower electron density). Therefore, as the sphere of electron density d2 (low with respect to the high electron density d1 of the ball) exhibits a rotational symmetry, if the section of the radiation beam is lower than the diameter of the sphere, the rotation of the beam around the sphere will be invisible on the detector, and the methods for detecting the beam edges and the ball center will be strictly the same, whatever may be the angle of incidence and the beam orientation. Moreover, as the diameter of the lower electron density sphere is larger than the beam section, the beam edges will be easily located on the detector because this locating will not interfere with the image of the limits of the sphere which will thus be invisible.

Likewise, as the beam section is larger than the diameter section of the ball, the ball of electron density d1 will be easily located on the detector without interfering with the detection of the beam edges.

The diameter section of the sphere must be larger than the beam section, i.e. the sphere diameter must be larger than the diameter of the beam if the beam has a circular section, or than the diagonal of the beam if the beam has a square section.

Preferably, the diameter of the sphere will be 20 mm larger than the section of the beam.

The diameter section of the ball must be lower than the beam section, i.e. the ball diameter must be lower than the beam diameter if the beam has a circular section, or than the beam diagonal if the beam has a square section. Preferably, the ratio between the diameter section of the ball and the beam section will be 1/10.

Advantageously, the material of electron density d2 will have an electron density close to the electron density of human living tissues, and especially a relative electron density (with respect to water) of about 1.15.

Thus, with this phantom object, the diameter of the ball in a material of electron density d1 is kept sufficiently low so that it can be contained in a small section radiation beam, thus not much subjected to variations of its sizes depending on the stand rotation, the means for positioning-aligning being supported by a sphere in a material of electron density d2 with a diameter sufficient on the one hand to support means which allow the operator to place/position accurately to the naked eye the phantom object in the treatment device, and, on the other hand, to contain all the small section of the radiation beam used for the tests.

The sphere in a material of electron density d2 can especially have a big size (about 500 $cm^3$). The locating means can be laser layers projected by laser projectors, for example red-colored or green-colored, positioned in the treatment room.

The means for aligning/positioning the sphere in a material of electron density d2 supported by the sphere thus allow an accurate positioning of the sphere with respect to the locating means consisting in three locating laser layers, given that the size of the sphere in a material of electron density d2, larger than the size of the ball in a material of electron density d1, allow an easy and accurate visual positioning/placement of the phantom object with respect to the locating laser layers by the operator performing the quality control test, this placement being controlled on a length (the diameter of the sphere) longer than for the phantom objects of the prior art (diameter of the ball).

The material of electron density d2 from which the sphere (8) is made can be a plastic material, in particular a plastic material transparent for the visible light, especially in poly (methylmethacrylate) (PMMA). Thus, one can visually ensure the proper positioning of the ball in a material of electron density d2 in the center of the sphere. The material of electron density d2 of the sphere allows for the sphere to be invisible on the radiography images acquired during the test, only the ball in a material of electron density d1 in the center being visible on these images.

According to a specific feature of the invention, the means for aligning/positioning the sphere can consist in three visible equatorial lines orthogonal pairwise, provided on the surface of the sphere in a material of electron density d2, said lines being represented physically by a painted or printed line, or by an engraved groove. Thus, the visible lines allow the visual checking, during the placement of the phantom object, of the orthogonality, the spatial position (horizontality and verticality) and the coincidence of the laser layers, which must be aligned with the visible lines of the object.

According to another specific feature of the invention, the means for aligning-positioning the sphere can comprise additionally, on either side of each equatorial line, additional visible lines, advantageously discontinuous, parallel to the three equatorial lines, wherein said additional visible lines are represented physically by a painted or printed line, or by an engraved groove and said additional visible lines are formed at a preset spacing from the associated equatorial line, so that an alignment of the locating means on said additional visible lines provides a visual indication of the position of the ball in a material of electron density d1 with respect to the point of convergence of the three axes (V', H', C').

Thus, as the spacing between the additional visible lines is known, the operator can deduct than, when those are aligned with the locating means, the position of the ball in a material of electron density d1, and hence the correction to make to the placement of the phantom object, without other measurement device.

According to a specific feature of the invention, when the locating means are laser layers emitted by laser projectors, the visible lines and, when provided, the additional visible lines, can be covered with a substance adapted to reflect the light in the visible spectrum, to be enlightened with the same color as the color of the laser layers, when said visible lines, and when provided, when said additional visible lines, are aligned with the laser layers.

For example, the visible lines can advantageously be clear-colored or white. Thus, the visual confirmation of the alignment of the visible lines and of the locating means, by light reflection, is easier for the operator.

The visible lines, and, when provided, the additional visible lines, can be made in strip-shaped equatorial areas of the surface of the sphere, which have been treated to absorb or to diffuse light in the visible spectrum. The visual confirmation of the alignment of the visible lines, of the additional visible lines when provided, with the locating means is then still enhanced, as the light of the locating means is reflected on the visible lines, and absorbed or diffused outside these visible lines.

According to a specific feature of the invention, the strip-shaped areas can be formed by grinding or by a dark colored paint.

The dark color can, for example, be black.

Thus, when the locating means are laser layers and the visible lines are clear colored, the visible lines reflect laser light when they are aligned with the laser layers, while, in the grinded or dark-colored strip-shaped areas, laser light is diffused or absorbed.

According to another specific feature of the invention, the sphere diameter can be selected sufficiently large so that the means for visual aligning-positioning can be distinguished without difficulty by the human eye, the diameter of said sphere being especially between 80 and 200 mm, the visible lines, and, when provided, the additional visible lines having a width between 0.1 mm and 0.5 mm, particularly of 0.2 mm, and the additional visible lines, when provided, being spaced by 1 mm on either side of each equatorial visible lines, and the strip-shaped areas, when provided, having a width between 2 mm and 10 mm, preferably of 5 mm, the ball having a diameter between 5 and 6 mm.

Thus, when the laser layers are outside the visible lines, the laser layers diffuse in the grinded strip-shaped area or are absorbed in the dark-colored strip-shaped area. For example, with a 5 mm wide strip-shaped area, and 0.2 mm wide equatorial visible lines and additional visible lines, with a 1 mm spacing between each visible line, in each strip-shaped area can be positioned an equatorial visible line and two additional visible equatorial lines on either side of each equatorial visible line. Thus, as soon as the laser layers are on one of the five visible lines, the laser layers do not diffuse anymore or are not absorbed anymore in the strip-shaped areas, and this visible line enlightens. The white color is preferably selected for the visible lines to make this system as efficient with green laser layers as with red laser layers. Moreover, grinding or darkening a 5 mm strip-shaped area prevents the laser layers of one side and entering into the transparent sphere from being subjected to a diffraction and thereafter being output on the other side of the sphere and interfering with the alignment of a laser layer (contralateral laser layer).

Thus, given the spherical form of the phantom object and its rotational symmetry, it is ensured that the form of the sphere made in material of electron density d2 (plastic material) will have no influence on the recorded image of the ball in a material of electron density d1, during any rotation of the device around any one of the three axes of the treatment device, as the thickness of the sphere-shaped phantom object which is passed through is always the same. Therefore, this geometry results in homogenous recurrent radiographies, which facilitates the computer-assisted methods of automatic detection of the ball center and of the radiation beam boundaries and improves their accuracy.

Advantageously, the ball in a material of electron density d1 can be in tungsten.

According to an advantageous feature of the phantom object of the present invention, the placing means can consist in a rod-like or tube-like metal elongated element, for example in titanium or aluminium, an end of which is to be inserted in a hole made in the sphere and to be secured therein for example by screwing, and in a plate which is attached at the other end of the elongated element and which is arranged to act as a counter-weight to the phantom object and to the elongated element when the plate is positioned on the upper plane of the patient support and to be able, therefrom, to be oriented for the placement of the phantom object at the point of convergence of the three axes (V', H', C').

The plate can be provided with means for adjusting the level of said plate with respect to the plane of the patient support during the placement of the phantom object. These means can in particular be leveling screws.

According to particular features of the invention, the plate has a thickness between 20 and 40 mm, preferably 20 mm, a width between 50 and 200 mm, preferably 80 mm, and a length between 200 and 500 mm, preferably 300 mm, the elongated element has a length between 50 and 300 mm, preferably 100 mm, wherein the elongated element can be inserted in the plate over a length between 20 and 80 mm, preferably 50 mm.

When the elongated element is a rod, its diameter is between 5 and 15 mm, and is preferably 10 mm at most.

The sphere can be provided with a radial channel with a diameter slightly larger than the one of the ball, wherein said channel is plugged by a rod made of a material of electron density d2, which can protrude out the surface of the sphere, and the elongated element can be adapted to be connected to the sphere by screwing at the periphery of the rod wherein said elongated element can comprise an axial recess shaped complementarily to the shape of the rod when said rod is protruding, in order to accommodate this protruding part.

In this case, the protruding rod is used for reinforcing the support of the sphere on the elongated element. It has a diameter between 2 and 10 mm, preferably 8 mm, and a length between 60 and 120 mm, preferably 70 mm.

According to a preferred feature of the phantom object, the elongated element can be secured to the sphere, at the intersection of two equatorial visible lines.

The invention relates also to a method for the manufacture of a phantom object as defined above, characterized in that the method comprises the steps of:

providing a sphere in a material of electron density d2 and digging with a ball end mill, whose diameter is equal to the one of the spherical ball in a material of electron density d1, a cylindrical channel from a point at the surface of the sphere, along a radius thereof, by digging the sphere beyond the center thereof over a distance equal to half the diameter of the ball in a material of electron density d1;

inserting said ball up to the bottom end of this channel;

plugging the remaining hole with a rod in a material of electron density d2 with a diameter equal to the one of said ball, at the end of which was dug the complementary/reciprocal shape of the half ball, wherein the rod is then stuck in the channel with an adhesive material of electron density d2, and the rod can protrude out the surface of the sphere;

forming a portion with a larger diameter and internally threaded in the vicinity of the surface of the sphere, at the base of the protruding portion of the rod when said rod is protruding;

screwing an elongated element having at one end an external thread over the internal thread of the sphere, wherein the elongated element is provided optionally with an axial recess for accommodating the protruding portion of the rod when said rod is protruding;

attaching the other end of the elongated element to a plate;

optionally forming the strip-shaped equatorial areas either by grinding with a 3D machine tool or by a dark colored paint, adapted to diffuse or absorb the wavelengths in the visible spectrum, advantageously so that the elongated element is secured to the sphere at the center of the overlapping area between two strip-shaped equatorial areas;

forming the visible lines and, when provided, the additional visible lines by engraving or printing on the surface of the sphere with a 3D machine-tool, advantageously so that the elongated element is secured to the sphere at the point of convergence of two equatorial visible lines; and optionally coloring the visible lines and, when provided, the additional visible lines by painting them by hand with a paint brush.

The elongated element can be a filled rod, in which case the rod in a material of electron density d2 does not protrude out the sphere, the elongated element being then only secured to the sphere by screwing.

The elongated element can also be a hollow tube, for reducing the weight of the set phantom object-rod.

The fact that the elongated element has an axial recess cooperating with the protruding part of the rod in a material of electronic density d2 reinforces the support of the sphere on the elongated element and can advantageously be used as a guide for the procedure of formation of the portion with a larger diameter having an internal thread in the vicinity of the surface of the sphere.

The invention also relates to a method of checking the coincidence, the orthogonality and the spatial position of the locating means of the three theoretical axes of rotation (V', H', C') of a device for radiation therapy treatment in a suitable room, the room and/or radiation therapy device being provided with means for locating these three theoretical axes (V', H', C') characterized in that it comprises the steps of:

activating the locating means of the three theoretical axes (V', H', C') for visually representing the three theoretical axes (V', H', C');

placing a phantom object as defined above at the observed point of convergence or isocenter (G') of the three theoretical axes (V', H', C');

visually observing whether each of the locating means of the three theoretical axes (V', H', C') follow the corresponding respective aligning-positioning means on the phantom object;

depending on the observed difference(s), modify the setting of the locating means to have the locating means of the theoretical axes (V', H', C') follow the corresponding respective aligning-positioning means on the phantom object, in order to ensure the coincidence, the orthogonality and the spatial position of the locating means of the three theoretical axes.

When the phantom object is placed on the patient support having a null rotation angle, the sagittal layer is vertical and in the longitudinal direction of the patient support, the two transverse layers are in the same plane, orthogonal to the plane of the sagittal layer and vertical, and the frontal layers are in the same plane.

The invention also relates to a method of searching the isocenter of a device of radiation therapy treatment, using a phantom object as defined above, wherein external and/or device-supported means are provided to represent visually the three theoretical rotation axes (V', H', C') of the device, wherein the method is characterized in that it comprises the steps of:

checking the coincidence, the orthogonality and the spatial position of the locating means of the three theoretical axes (V', H', C') according to the method defined above;

while the phantom object stays at the theoretical isocenter (G'), irradiating the phantom object with a radiation beam emitted from the collimator, wherein said beam is detected by the radiation detecting means of the treatment device, and the irradiation is performed at various positions of the patient support, of the stand and of the collimator around each of their axes of rotation (V, H, C);

analyzing the resulting images;

determining the real position of the three axes of rotation (V, H, C) and their point of convergence (G), real isocenter of the device for radiation therapy treatment;

adjusting the locating means (5, 6) of the three theoretical axes (V', H', C') so that the real isocenter (G) and the theoretical isocenter (G') match.

The present invention also relates to a radiation therapy device equipped with the phantom object as defined above.

BRIEF DESCRIPTION OF THE SEVERAL VIEWS OF THE DRAWING

In order to better illustrate the subject-matter of the present invention, two preferred embodiments are described thereafter, together with the accompanying drawings on which.

DETAILED DESCRIPTION OF THE INVENTION

FIG. 3 shows a conventional device for radiation therapy treatment, in a radiation therapy treatment room.

This device comprises, conventionally, a structure which comprises at least a vertical wall P supporting a stand 1, and a table or patient support 2.

On this vertical wall P, the stand 1, substantially C-shaped in a lateral view, is conventionally mounted rotationally movable around a horizontal axis. The stand 1 bears at one end an irradiation head which ends by a collimator 3, and at the other end, opposite the collimator 3 and facing it, a device for detecting the radiation 4 emitted from the collimator 3, this device of radiation detection being referred as portal imager 4, which allows to acquire frames of the radiation emitted from the collimator 3, and to perform the computer processing of the frames.

The stand 1 is rotationally movable at 360° around a horizontal axis H, as shown on FIG. 3, wherein the horizontal axis H substantially passes through the middle of the portion in the vertical plane of the stand 1. The null rotation angle of the stand 1 corresponds to the vertical position of the stand 1, as shown on FIG. 4.

The collimator 3, conventionally for the devices for radiation therapy treatment, has an axis C of rotation about itself, said axis of rotation passing through the center of the collimator 3, and having the direction of the radiation emitted from the collimator 3.

The table or patient support 2 also has a vertical axis of rotation V, passing through the center of the collimator 3 when the stand 1 has a null rotation angle, and allows the movement of the patient with respect to the stand to irradiate the patient over various areas. The null rotation angle of the patient support 2 corresponds to the position of the patient support 2 in which the horizontal axis of rotation H of the stand 1 is parallel to the longitudinal direction of the patient support 2.

Figure 4:
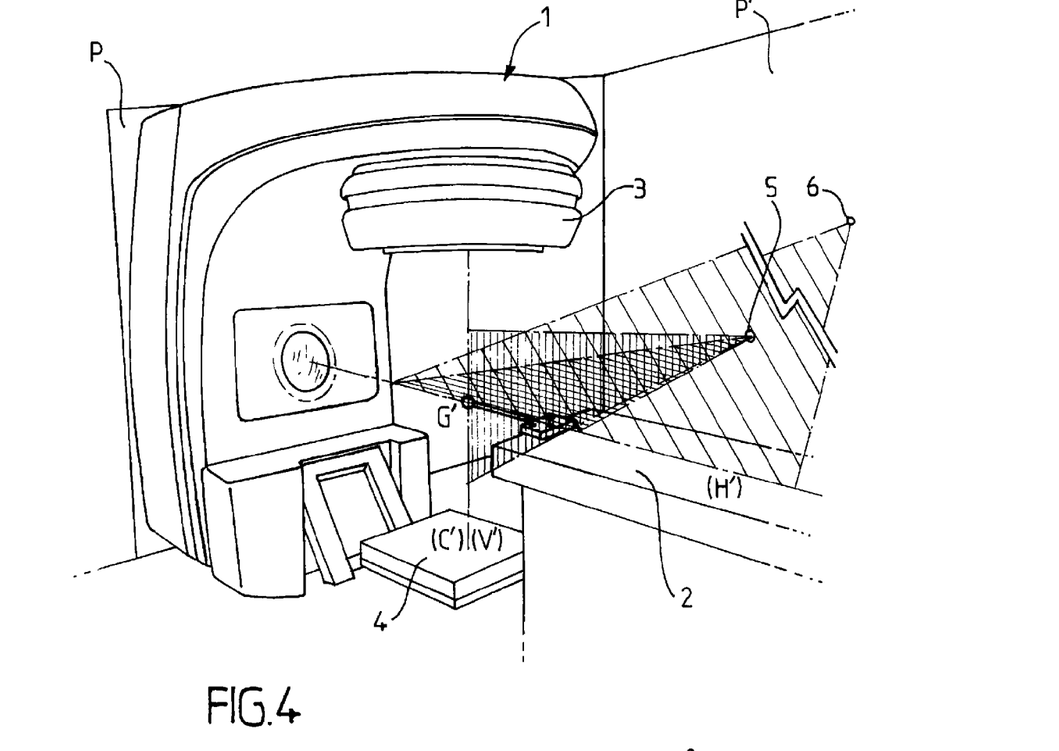
FIG. 4 shows a view similar to FIG. 3, wherein the phantom object is in a use position, and wherein the locating means visually and physically represent the three theoretical axes of rotation of the device for radiation therapy treatment.

Thus, when the rotation angle of the stand 1 is null, as it is shown, for example on FIG. 4, ideally, the axis of rotation C of the collimator 3 and the axis of rotation V of the patient support 2 are coincident.

The intersection of the three axes of rotation H, V, C forms the real isocenter G of the device for radiation therapy treatment.

Turning now to FIG. 4, the device for radiation therapy treatment of the FIG. 3 is shown in a position in which the rotation angle of the stand 1 is null, and the rotation angle of the patient support 2 is null.

As shown on FIG. 4, laser projectors 5, 6 are provided, on the one hand on a wall P', orthogonal to the wall P supporting the stand 1, and on the other hand on the wall facing the wall P, to project laser layers, represented by hatching lines on FIG. 4. It should be noted that the wall facing the wall P', which is not shown to make the reading of FIG. 4 easier, supports a laser projector identical to the laser projector 5 supported by the wall P', both laser projectors facing each other and projecting in the same planes laser layers in direction of the phantom object, these planes being defined hereafter relative to the laser projector 5. Hence there are in all five laser layers projected, three being shown on the drawing to make its reading easier.

These laser layers are useful for positioning the theoretical isocenter G' of the device for radiation therapy treatment.

The laser projector 5 positioned in the wall P', substantially at the level of the upper surface of the patient support 2, projects two orthogonal laser layers.

The first laser layer has a horizontal plane and is called frontal layer, and the second laser layer, called transverse layer, has a vertical plane perpendicular to the plane of the frontal layer, and to the plane of the wall comprising the laser projector 5.

The laser projector 6, shown schematically on FIG. 4, is positioned on the wall (not shown to make the reading of the drawing easier) opposite to the wall P, and projects a vertical laser layer, called sagittal layer, whose plane is perpendicular to the respective planes of the first and second layers, and which forms the intermediate plane in the longitudinal direction of the patient support 2, when the rotation angle of the patient support 2 is null, as shown on FIG. 4.

The intersection of the sagittal and frontal layers defines the theoretical axis of rotation H' of the stand 1, while the intersection of the sagittal and transverse layers defines the theoretical axes of rotation of the collimator 3 C' and of the patient support 2 V', when the rotation angle of the stand 1 is null.

The intersection of the three laser layers projected by the laser projectors 5 and 6 (and by the laser projector supported by the wall facing the wall P', not shown) hence defines the theoretical isocenter G' of the device for radiation therapy treatment.

This theoretical isocenter G' is useful for representing, for the operator, the position of the center of the tumor to be treated on the patient. For an optimal treatment of the tumor, i.e. a maximum of rays on the tumor and a minimum on the tissues around the tumor, both isocenters G and G' have to match, as indicated above.

The real isocenter G, set by the mechanical features of the treatment device, cannot be moved by the operator.

The theoretical isocenter G' is hence set by adjusting the laser layers for corresponding to the real isocenter G.

As indicated above, the superposition of these two isocenters G and G' is performed by means of the Winston & Lutz test, which consists in positioning a ball in a material of high electron density d1, in the presented embodiment, in tungsten, to the theoretical isocenter G', in acquiring images of this ball by the device for radiation therapy treatment, and in analyzing the resulting images of the ball to determine the shift between both isocenters G and G'.

The position of the theoretical isocenter G' is corrected by adjusting the laser layers, until the position of the theoretical isocenter G' matches the position of the real isocenter G.

As underlined above, it is also important, during this adjustment, that the five laser layers are orthogonal pairwise.

Figure 1:
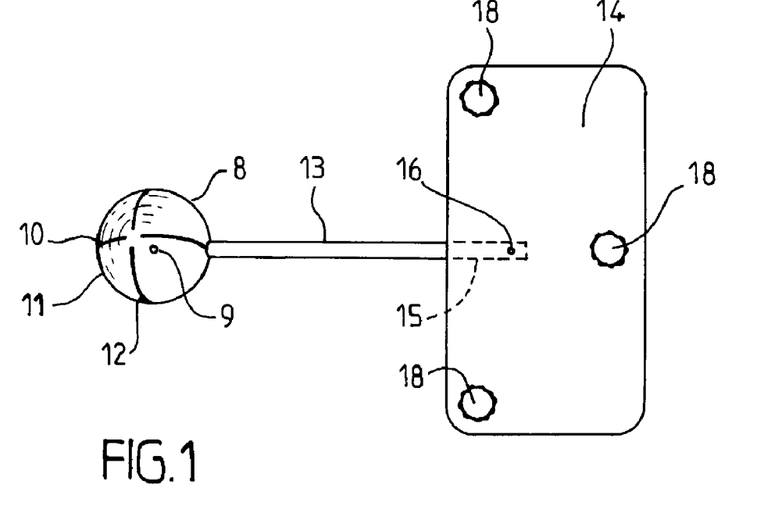
FIG. 1 is a top view of the phantom object according to the present invention, attached to its support.
Figure 2:
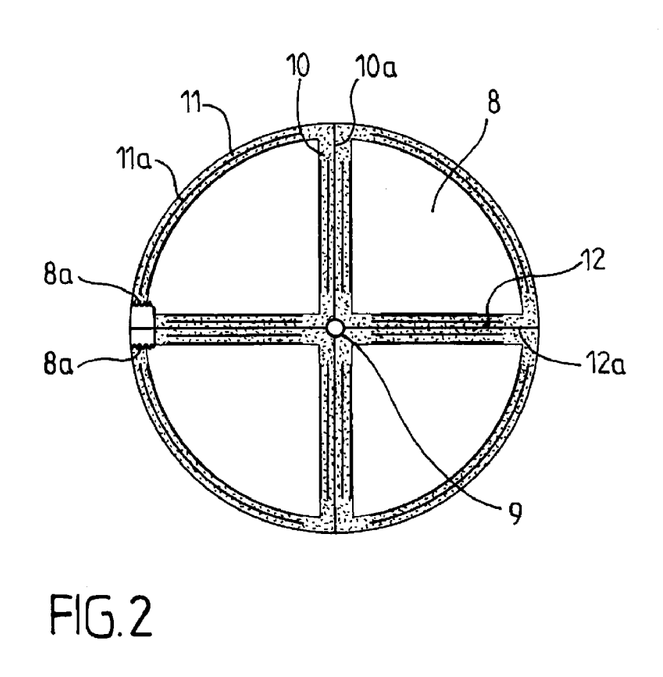
FIG. 2 is a schematic view of the surface of the phantom object of FIG. 1.
Figure 5:
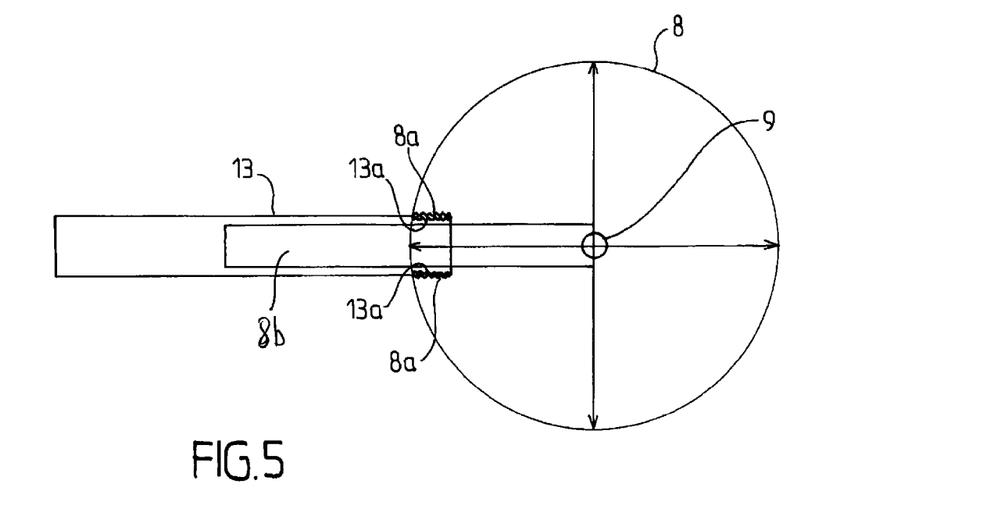
FIG. 5 is a schematic representation of the phantom object.

The phantom object of the present invention used for performing this test is shown on FIGS. 1, 2 and 5.

It consists in a filled sphere 8 in a material of electron density d2 (d2 corresponding to a relative electron density of 1.156), such as poly(methylmethacrylate) (PMMA), with a diameter of 80 to 200 mm.

At the center of this sphere 8 is embedded a spherical ball 9 in a material of electron density d1, such as tungsten, wherein the ball 9 has a diameter of 5 mm and the electron density d1 of tungsten corresponds to a relative electron density of 13.995.

A rod 8b made of the same material of electron density d2 as the sphere 8 protrudes out the sphere 8 from the center thereof, wherein the rod 8b has the direction of a radius of the sphere 8.

Three strip-shaped areas 10, 11, 12, called bottom strips are formed at the surface of the sphere 8.

The three bottom strips 10, 11, 12 are pairwise orthogonal equatorial strips, each bottom strip 10, 11, 12 being formed by grinding the sphere surface or painting the sphere surface with a dark color on a 5 mm wide equatorial peripheral strip.

The bottom strips 10, 11, 12 absorb or diffuse light in the visible spectrum.

The sphere 8 is provided with three sets of equatorial visible lines 10a, 11a, 12a, the visible lines being represented physically in this embodiment by grooves, the sets of lines being pairwise orthogonal, and engraved on the surface of the sphere 8, at the center of each respective bottom strip 10, 11, 12, each set of grooves 10a, 11a, 12a, having the same direction than the respective bottom strip 10, 12, 12 in which it is formed.

Each set of grooves 10a, 11a, 12a comprises a continuous equatorial groove, along the whole circumference of the sphere 8, as well as several auxiliary grooves, parallel to the equatorial groove, and located symmetrically on either side of the equatorial groove, with a 1 mm spacing between each groove.

The grooves of each set of grooves 10a, 11a, 12a, are covered with a white-colored material, for example a paint, reflecting light in the visible spectrum, and 0.2 mm wide. Each set of grooves 10a, 11a, 12a is provided with a central equatorial groove and two auxiliary grooves from either side of the equatorial groove, the grooves in each bottom strip being spaced by 1 mm.

The bottom strips 10, 11, 12 and the sets of grooves 10a, 11a, 12a are arranged so that the protruding portion of the rod 8b is located at the intersection of two equatorial grooves, and hence at the intersection of two bottom strips 10, 11, 12.

As is shown on FIGS. 1 and 5, a rod-like elongated element 13 in metal, such as titanium or aluminium, is provided at one end with an external thread 13a, said rod 13 comprising at this end, an axial recess complementary shaped with respect to the protruding portion of the rod 8b. The rod 13 is fit into the protruding portion of the rod 8b and screwed by screwing to an thread 8a on the sphere 8 near its surface, at the basis of the protruding portion of the rod 8b.

A support 14, consisting in a rectangular plate in dense plastics (such as polyoxymethylene sold under the commercial name DELRIN®) with rounded edges, 20 mm thick, has on one of its thick sizes a bore 15, into which the other end of the rod 13 is attached.

A through hole 16 is made through the thickness dimension of the support 14, at the internal end of the bore 15, the hole 16 allowing the transverse passage of a metallic axis, in order to block in position the rod 13 and to avoid any movement of rotation with respect to the support 14 of the rod 13, and hence of the sphere 8.

The support 14 is further provided with leveling screws 18, to set the height and the inclination of the support 14 with respect to the upper surface of the patient support 2 on which it rests during the test of Winston-Lutz.

When the support 14 is positioned properly on the patient support, especially centered and leveled, a first equatorial groove is in the mean plane of the support, hence horizontal, a second equatorial groove is vertical, in the axis of the rod 13, the third equatorial groove being orthogonal to the two other, vertical.

When used for the Winston-Lutz test, the phantom object consisting in the sphere 8, is attached by screwing of the threads 8a of the sphere 8 and 13a of the rod 13, the rod 13 being itself attached to the support 14, so that at least one of the equatorial grooves of one set of grooves 10a, 11a, 12a is part of the mean plane of the support 14, as shown on FIG. 1.

As indicated on FIG. 4, the support 14 rests at the end of the patient support 2 which faces the stand 1, so that only the support 14 rests on the upper surface of the patient support 2, the rod 13 and the sphere 8 being cantilevered above the portal imager 4.

The laser projectors 5 and 6 (as well as the laser projector not shown facing the laser projector 5) are then activated, in order to project the sagittal, frontal and transverse laser layers.

The position of the sphere 8 is adjusted so that each equatorial groove of each set of groove 10a, 11a, 12a is aligned on one of the five laser layers. If the laser layers are not rigorously pairwise orthogonal, which can be found when the sphere 8 cannot be positioned simultaneously on the five layers so that each equatorial groove of each set of grooves 10a, 11a, 12a corresponds to a respective laser layer, then the projectors 5, 6 must be adjusted in order to respect this orthogonality of the five laser layers.

If the laser layers are not aligned on one of the white grooves of each set of groove 10a, 11a, 12a engraved on the surface of the sphere 8 in the bottom strips 10, 12, 12, the lasers diffuse or are absorbed in the respective bottom strip 10, 11, 12. If, on the contrary, the laser layers are aligned on one of the white grooves, then the lasers do not diffuse anymore or are not absorbed by the bottom strip 10, 11, 12, but are reflected by the white groove, and the white groove takes the color of the laser layer, red or green in the case of most of the used lasers.

Once the sphere 8 is properly positioned at the intersection of the five laser layers, the actual Winston Lutz test, as indicated above, can start, the sphere 8 being positioned at the theoretical isocenter G', as shown on FIG. 4.

It should be noted that other support means for the sphere 8 could be considered, without departing from the scope of the present invention.

The method for manufacturing of the phantom object is as follows: a sphere 8 in PMMA with a diameter of 100 mm is provided and, with a ball end mill with a diameter of 5 mm, a cylindrical channel is dug from a point (pole) at the surface of the sphere 8, along a radius thereof, by digging the sphere 8 2.5 mm beyond the center thereof.

A ball 9 in tungsten with a diameter of 5 mm is inserted in this channel to its bottom.

The remaining hole is then plugged by a rod 8b in PMMA with a diameter of 5 mm at the end of which was dug the shape complementary to the one of the half ball 9 in tungsten, which allows the rod 8b to fill perfectly the channel dug in the sphere 8. The rod 8b is then stuck in the channel with a special adhesive for PMMA.

A portion of larger diameter with an internal thread near the surface of the sphere 8 is then formed, at the base of the protruding portion of the rod 8b, the rod 8b protruding out the sphere of about 8 to 40 mm.

A screw 13 bearing at one end an external thread is then screwed on the internal thread 8a of the sphere 8, the rod 13 being a filled rod comprising an axial recess for accommodating the protruding portion of the rod 8b.

The engagement of the rod 8b in the recess of the rod 13 reinforces the support of the sphere on the rod 13, and can be used as a guide for the procedure consisting in forming the internal thread on the sphere.

The other end of the rod 13 is then attached to a plate 14, then optionally the strip-shaped areas 10, 11, 12 are formed either by grinding with a 3D machine-tool, or by a dark-colored paint, for example, black-colored, adapted to diffuse or absorb wavelengths in the visible spectrum, advantageously such that the rod 13 is positioned at the center of the overlapping area between two strips-shaped areas 10, 11, 12.

The visible lines and, when provided, the additional visible lines 10a, 11a, 12a are then formed by engraving or printing on the surface of the sphere 8 with a 3D machine-tool, advantageously such that the rod 13 is positioned at the point of convergence of the two equatorial visible lines, and optionally, the visible lines and, when provided, the additional visible lines 10a, 11a, 12a are colored by painting them by hand with a paint brush, for example with white or clear-colored paint, reflecting the wavelengths in the visible spectrum.

The latter procedures can, if necessary, be realized by putting the sphere 8 in rotation around the aluminium support tube 13.

The invention claimed is:

1. A phantom object for a quality control test of a device for radiation therapy treatment, comprising:
    a spherical ball made of a material having an electron density d1, and a sphere made of a material having an electron density d2,
    wherein,
    the spherical ball is positioned at a center of the sphere,
    said ball has a diameter between 2 and 10 mm,
    said sphere has a diameter between 80 and 200 mm, and
    a ratio of the electron density d1 and the electron density d2 is greater than or equal to 1.1,
    and wherein,
    said sphere includes on its outer surface a visual alignment means for positioning the phantom object, said means comprising three visible equatorial lines orthogonal pairwise, formed on the surface of the sphere, and
    said sphere comprises a means for securing the sphere to a placing means for placing the phantom object on the device for radiation therapy treatment.

2. The phantom object according to claim 1, wherein the material of electron density d2 from which the sphere is made is a plastic material, a plastic material transparent for the visible light, or poly(methylmethacrylate) (PMMA).

3. The phantom object according to claim 1, wherein the visual alignment means are represented physically by a painted or printed line, or by an engraved groove.

4. The phantom object according to claim 3, wherein the visual alignment means further comprise, on either side of each equatorial line, additional visible lines, parallel to the three equatorial lines, wherein said additional visible lines are represented physically by a painted or printed line, or by an engraved groove and said additional visible lines are formed at a preset spacing from an associated equatorial line.

5. The phantom object according to claim 4, wherein the visible lines and the additional visible lines are covered with a substance adapted to reflect light in the visible spectrum, to be illuminated with the same color as the color of laser layers, when said visible lines and said additional visible lines are aligned with the laser layers.

6. The phantom object according to claim 4, wherein the visible lines and the additional visible lines are provided in strip-shaped equatorial areas of the surface of the sphere, and said equatorial areas have been treated to absorb or to diffuse light in the visible spectrum.

7. The phantom object according to claim 6, wherein the strip-shaped equatorial areas are formed by grinding or by a dark colored paint.

8. The phantom object according to claim 6, wherein
the visible lines and, the additional visible lines have a width between 0.1 mm and 0.5 mm,
the additional visible lines are spaced by 1 mm on either side of each equatorial visible line, and
the strip-shaped areas have a width between 2 mm and 10 mm.

9. A method for the manufacture of a phantom object as defined in claim 6, wherein the method comprises the steps of:
providing a sphere in a material of electron density d2 and digging with a ball end mill, whose diameter is equal to the diameter of the spherical ball in a material of electron density d1, a cylindrical channel from a point at the surface of the sphere, along a radius thereof, by digging the sphere beyond the center thereof over a distance equal to half the diameter of the ball in a material of electron density d1;
inserting said ball up to a bottom end of said channel;
plugging the remaining hole with a rod in a material of electron density d2 with a diameter equal to the one of said ball, at the end of which was dug the complementary shape of the half ball, wherein the rod is then stuck in the channel with an adhesive material of electron density d2, and the rod can protrude out the surface of the sphere;
forming a portion with a larger diameter and internally threaded in the vicinity of the surface of the sphere, at the base of the protruding portion of the rod when said rod is protruding;
screwing an elongated element having at one end an external thread over the internal thread of the sphere, wherein the elongated element is provided optionally with an axial recess for accommodating the protruding portion of the rod when said rod is protruding;
attaching the other end of the elongated element to a plate;
optionally forming the strip-shaped equatorial areas either by grinding with a 3D machine tool or by a dark colored paint, adapted to diffuse or absorb the wavelengths in the visible spectrum, advantageously so that the elongated element is secured to the sphere at the center of the overlapping area between two strip-shaped equatorial areas;
forming the visible lines and, when provided, the additional visible lines by engraving or printing on the surface of the sphere with a 3D machine-tool, advantageously so that the elongated element is secured to the sphere at the point of convergence of two equatorial visible lines; and
optionally coloring the visible lines and, when provided, the additional visible lines by painting them by hand with a paint brush.

10. The phantom object according to claim 4, wherein the additional visible lines are discontinuous.

11. The phantom object according to claim 1, wherein the material of electron density d1 is tungsten.

12. The phantom object according to claim 1, wherein the placing means comprises a rod-like or tube-like metal elongated element, the metal being titanium or aluminium, an end of which is to be inserted in a hole provided in the sphere and to be secured therein by screwing, and in a plate which is attached at the other end of the elongated element and which is arranged to act as a counter-weight to the phantom object and to the elongated element when the plate is positioned with respect to the device for radiation therapy treatment.

13. The phantom object according to claim 12, wherein the plate is provided with means for adjusting a level of said plate with respect to a plane of a patient support of the device for radiation therapy treatment during the positioning of the phantom object.

14. The phantom object according to claim 12, wherein the sphere comprises a radial channel having a diameter slightly larger than the diameter of the ball, said channel being plugged by a rod made of a material having electron density d2, which can protrude out from the surface of the sphere, and
the elongated element is adapted to be connected to the sphere at the periphery of the rod, said elongated element comprising an axial recess shaped complementarily to the shape of the rod when said rod is protruding out from the surface of the sphere, in order to accommodate this protruding part.

15. The phantom object according to claim 12, wherein the elongated element is secured to the sphere at an intersection of two equatorial visible lines.

16. The phantom object according to claim 1, wherein said ball has a diameter between 5 and 6 mm.

17. A method of checking the coincidence, orthogonality and position in a treatment room space of a locating means of the isocenter of a device for radiation therapy treatment, wherein said isocenter is an intersection point of three theoretical rotation axes (V', H', C') of the device for radiation therapy treatment, wherein the method comprises the steps of:
activating the locating means of the three theoretical axes (V', H', C') for visually representing the three theoretical axes (V', H', C');
positioning a phantom object as defined in claim 1 at an observed point of convergence or isocenter (G') of the three theoretical axes (V', H', C');
visually observing whether each of the locating means of the three theoretical axes (V', H', C') follow a corresponding respective visual alignment means on the phantom object; and then,
depending on one or more visually observed difference(s), modifying a setting of the locating means to have the locating means of the theoretical axes (V', H', C') follow the corresponding respective visual alignment means on the phantom object, in order to ensure the coincidence, the orthogonality and the spatial position of the locating means of the three theoretical axes (V', H', C').

18. A method of searching the isocenter of a device for radiation therapy treatment, using a phantom object for a quality control test of a device for radiation therapy treatment, said phantom object comprising a spherical ball made of a material having an electron density d1, and a sphere made of a material having an electron density d2,
wherein,
the spherical ball is positioned at the center of the sphere,
said ball has a diameter between 2 and 10 mm,
said sphere has a diameter between 80 and 200 mm, and
a ratio of the electron density d1 and the electron density d2 is greater than or equal to 1.1,
and wherein,
said sphere includes on its outer surface a visual alignment means for positioning the phantom object, said mean comprising three visible equatorial lines orthogonal pairwise, formed on the surface of the sphere,
said sphere comprises a means for securing the sphere to a placing means for placing the phantom object on the device for radiation therapy treatment, and said phantom object comprises external and/or device-supported means for representing visually three theoretical axes (V', H', C') of the device and their intersection point or isocenter, wherein the method comprises the steps of:
 checking the coincidence, orthogonality and spatial position of the locating means of the three theoretical axes (V', H', C') according to the method of claim 15;
 while the phantom object stays at a theoretical isocenter (G'), irradiating the phantom object with a radiation beam emitted from a collimator, wherein said radiation beam is detected by a means for detecting radiation of the radiation therapy treatment device, and the irradiating is performed at various positions of a patient support, of a stand and of the collimator around each of their axes of rotation (V, H, C);
 analyzing images resulting from the irradiating;
 determining a real position of the three axes of rotation (V, H, C) and their point of convergence (G), which is a real isocenter of the device for radiation therapy treatment;
 adjusting the locating means of the three theoretical axes (V', H', C') so that the real isocenter (G) and the theoretical isocenter (G') match.

19. The method of searching the isocenter of a device for radiation therapy treatment according to claim 18, wherein said ball has a diameter between 5 and 6 mm.

* * * * *